US009451916B2

(12) United States Patent
Curtiss

(10) Patent No.: US 9,451,916 B2
(45) Date of Patent: Sep. 27, 2016

(54) SYSTEM AND METHOD FOR ASSESSING POSTURAL SWAY AND HUMAN MOTION

(75) Inventor: Chase Curtiss, Tulsa, OK (US)

(73) Assignee: SWAY MEDICAL LLC, Tulsa, OK (US)

( * ) Notice: Subject to any disclaimer, the term of this patent is extended or adjusted under 35 U.S.C. 154(b) by 1045 days.

(21) Appl. No.: 13/564,401

(22) Filed: Aug. 1, 2012

(65) Prior Publication Data

US 2013/0035613 A1    Feb. 7, 2013

Related U.S. Application Data

(60) Provisional application No. 61/514,211, filed on Aug. 2, 2011.

(51) Int. Cl.
| A61B 5/103 | (2006.01) |
| A61B 5/117 | (2016.01) |
| A61B 5/00 | (2006.01) |
| A61B 5/11 | (2006.01) |

(52) U.S. Cl.
CPC ............ *A61B 5/4023* (2013.01); *A61B 5/1116* (2013.01); *A61B 5/6898* (2013.01); *A61B 2503/10* (2013.01); *A61B 2562/0219* (2013.01)

(58) Field of Classification Search
CPC  A61B 5/6898; A61B 5/1116; A61B 5/4023; A61B 2503/10; A61B 2562/0219
USPC .................................................. 600/587, 595
See application file for complete search history.

(56) References Cited

U.S. PATENT DOCUMENTS

| 5,595,488 | A |  | 1/1997 | Gozlan et al. |
| 5,919,149 | A | * | 7/1999 | Allum ................... A61B 5/1116 600/595 |
| 5,961,332 | A |  | 10/1999 | Joao |
| 6,066,092 | A |  | 5/2000 | Cady et al. |
| 6,669,481 | B2 |  | 12/2003 | Winter et al. |
| 7,837,472 | B1 |  | 11/2010 | Elsmore et al. |
| 2006/0251334 | A1 |  | 11/2006 | Oba et al. |

(Continued)

FOREIGN PATENT DOCUMENTS

| WO | WO 01/54559 A2 | 8/2001 |
| WO | WO 01/54650 A2 | 8/2001 |

(Continued)

OTHER PUBLICATIONS

International Search Report for PCT/US2012/049333, mailed Nov. 14, 2012, Applicant: Capacity Sports, LLC.

*Primary Examiner* — Max Hindenburg
*Assistant Examiner* — Jonathan M Foreman
(74) *Attorney, Agent, or Firm* — Fellers, Snider, Blankenship, Bailey & Tippens, P.C.; Terry L. Watt

(57) ABSTRACT

There is provided herein a system and method for performing a balance evaluation that utilizes a hand held accelerometer that measures upper body compensatory and correctional movement. Instead of testing movement in the waist or lower extremity as is commonly done, the instant invention measures thoracic trunk sway to estimate an individual's balance via positional change algorithms. By holding the measuring device to the chest and performing one or a variety of balance tests, the instant invention can determine the amount of sway in the trunk without attached or fixed monitors, which presents a novel approach to assessing postural sway above the center of mass.

1 Claim, 2 Drawing Sheets

(56) References Cited

U.S. PATENT DOCUMENTS

| | | |
|---|---|---|
| 2008/0288200 A1 | 11/2008 | Noble |
| 2008/0306412 A1 | 12/2008 | Nieminen et al. |
| 2010/0176952 A1 | 7/2010 | Bajcsy et al. |
| 2011/0301435 A1* | 12/2011 | Albert ............... A61B 5/0404 600/301 |
| 2012/0184882 A1* | 7/2012 | Totman ............... A61B 5/1135 601/41 |

FOREIGN PATENT DOCUMENTS

| | | |
|---|---|---|
| WO | WO 01/72217 A1 | 10/2001 |
| WO | WO 2004/103176 A1 | 12/2004 |

* cited by examiner

FIGURE 1A    FIGURE 1B    FIGURE 1C
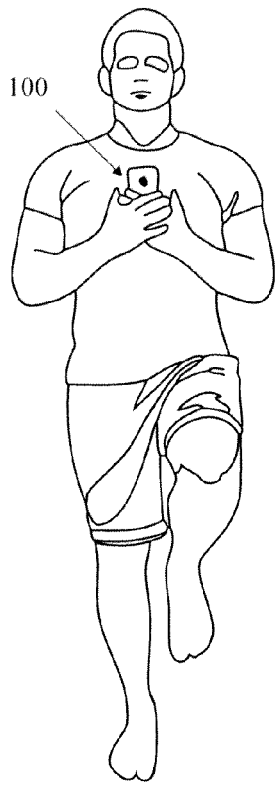
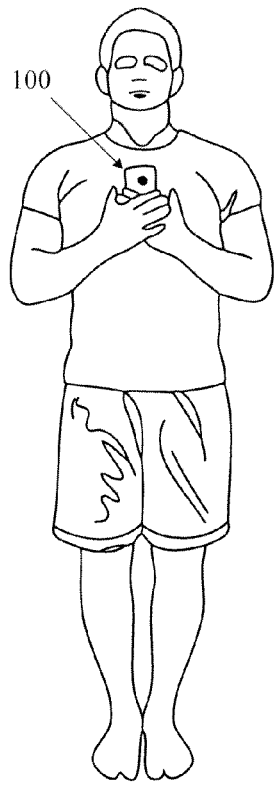
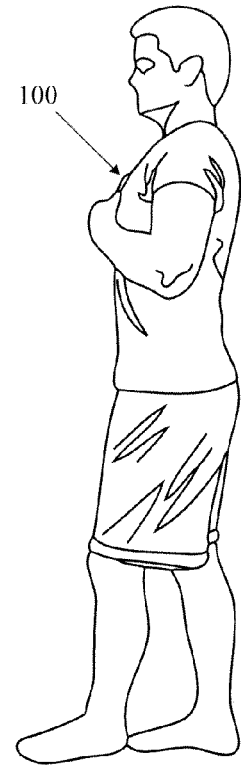
*Figure 3*
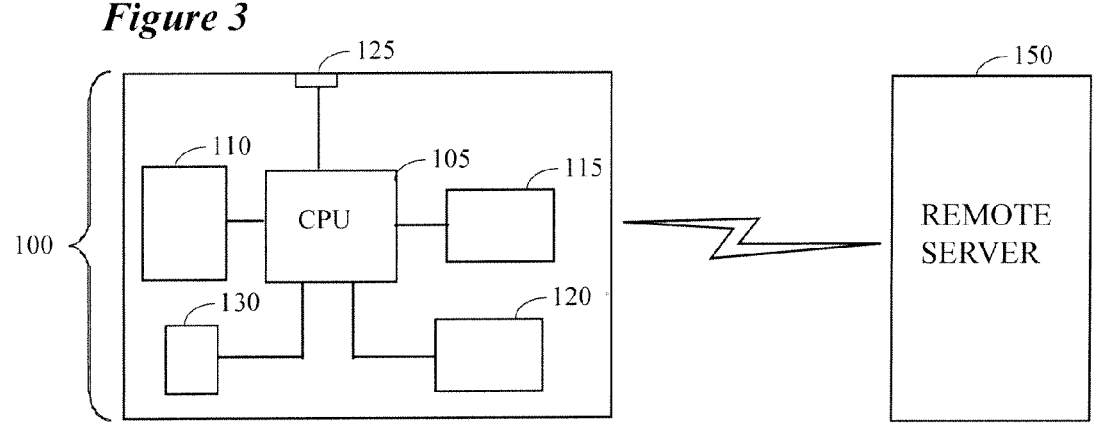

SYSTEM AND METHOD FOR ASSESSING POSTURAL SWAY AND HUMAN MOTION

CROSS REFERENCE TO RELATED APPLICATIONS

This application claims the benefit of U.S. Provisional Patent Application Ser. No. 61/514,211 filed on Aug. 2, 2011, and incorporates said provisional application by reference into this document as if fully set out at this point.

FIELD OF THE INVENTION

The present invention relates generally to the field of balance testing and, more particularly, postural sway and functional movement analysis as a function of a subject's loss of vestibular or stability control.

BACKGROUND OF THE INVENTION

The need for more accurate, accessible and cost effective assessments of balance and vestibular function are well documented by researchers and medical professionals. Current field evaluation tools for balance assessment utilize expensive force platforms, which are not practical for use in settings other than clinical research. Force platforms have also been questioned for their accuracy in the true evaluation of balance. The development of inexpensive electronic devices that can measure center of mass (COM) movements to estimate balance have been described in several clinical research projects, however the application of these tools within a server connected hand-held mobile device, for the purpose of evaluating medical conditions has been absent. The typical use of accelerometers to measure postural sway has been limited to lower body, waist or lumbar movement analysis and have not been used to analyze thoracic trunk sway. Thoracic sway presents a completely different measure of compensatory sway, because it analyzes above center of mass movement and therefore proprioceptive balance control of the lower extremity and the trunk without the false compensation of arm or head movement.

Balance testing has been identified as an important part of testing in fall risk prevention in the elderly, in prescription drug interaction, chronic neurological disease management, traumatic brain injury, stroke and performance testing in work readiness screening.

A multi-faceted approach, that incorporates various types of movement and postural stability measures, has long been needed to provide a true analysis of function and stability. Thus, the need exists for a portable, cost effective balance evaluation tool that measures the essential components of postural stability with specific equations developed to quantify changes in multiple testing conditions, acutely, and over time.

Heretofore, as is well known in the medical and balance assessment industry, there has been a need for an invention to address and solve the disadvantages of prior art methods. Accordingly it should now be recognized, as was recognized by the present inventors, that there exists, and has existed for some time, a very real need for a system and method that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of the invention within the ambit of the appended claims.

SUMMARY OF THE INVENTION

An embodiment of the instant invention is a hand-held balance evaluation system that employs a novel approach to measuring upper body compensatory and correctional movements for purposes of evaluating a subject's balance or dynamic movement without the need of a harnesses, or fixation techniques. The instant invention in some embodiments uses only a handheld computing device that instructs, measures, and analyzes a subject's motion via an accelerometer that is integral the computing device, and, in some embodiments, communicates with an external server for data analysis and live data interaction. Instead of testing movement in the waist or lower body extremity, which is the protocol used in any clinical research or previously marketed device using accelerometers, the instant invention measures anterior thoracic trunk sway to estimate an individual's balance using positional change algorithms. By asking the subject to hold the handheld device to the chest while one or a variety of balance tests are performed, an embodiment of the instant invention can determine the amount of sway in the trunk without attached or fixed monitors, which approach presents a novel protocol, testing device, and data analysis techniques for assessing postural sway.

In practice, the instant invention could be used, for example, on the sideline of a high school, college, professional, etc., contact sports event such as football. A participant who has been observed to have been involved in a head jarring collision can be provided with the hardware component of the instant invention and instructed to perform one or more simple movement tests, during which time the movement will be continuously measured by an accelerometer. The resulting suite of accelerometer readings are then used to calculate a coefficient that is reflective of the amount of postural sway observed during the test(s) which, in turn, can be compared with previous test scores obtained from the same individual and/or with population norms based on individuals that might be of approximately the same age, weight, gender, and/or physical condition, etc., to determine whether or not the that individual has symptoms that might be consistent with a concussion or other head injury. In such a case, the instant invention will preferably generate a signal that can be read by the sports participant and/or the coach, etc., which signal will indicate that further testing for a possible head injury is recommended. In a sports context, the individual would preferably not return to the game but instead be directed to report to a location where a medical diagnosis can be made. In other contexts (e.g., testing for Alzheimer's' disease, evaluating a patient who might be a fall risk, etc.) depending on the text results the individual might be referred to a specialist for more extensive testing.

The foregoing has outlined in broad terms the more important features of the invention disclosed herein so that the detailed description that follows may be more clearly understood, and so that the contribution of the instant inventors to the art may be better appreciated. The instant invention is not limited in its application to the details of the construction and to the arrangements of the components set forth in the following description or illustrated in the drawings. Rather the invention is capable of other embodiments and of being practiced and carried out in various other ways not specifically enumerated herein. Additionally, the disclosure that follows is intended to apply to all alternatives, modifications and equivalents as may be included within the spirit and the scope of the invention as defined by the appended claims. Further, it should be understood that the phraseology and terminology employed herein are for the purpose of description and should not be regarded as limiting, unless the specification specifically so limits the invention.

BRIEF DESCRIPTION OF THE DRAWINGS

Other objects and advantages of the invention will become apparent upon reading the following detailed description and upon reference to the drawings in which:

FIG. 1 illustrates embodiments of the instant invention as it might be used in practice.

FIG. 3 contains a high-level schematic illustration of a hardware component of the instant invention.

DETAILED DESCRIPTION OF THE PREFERRED EMBODIMENTS

Figure 2:
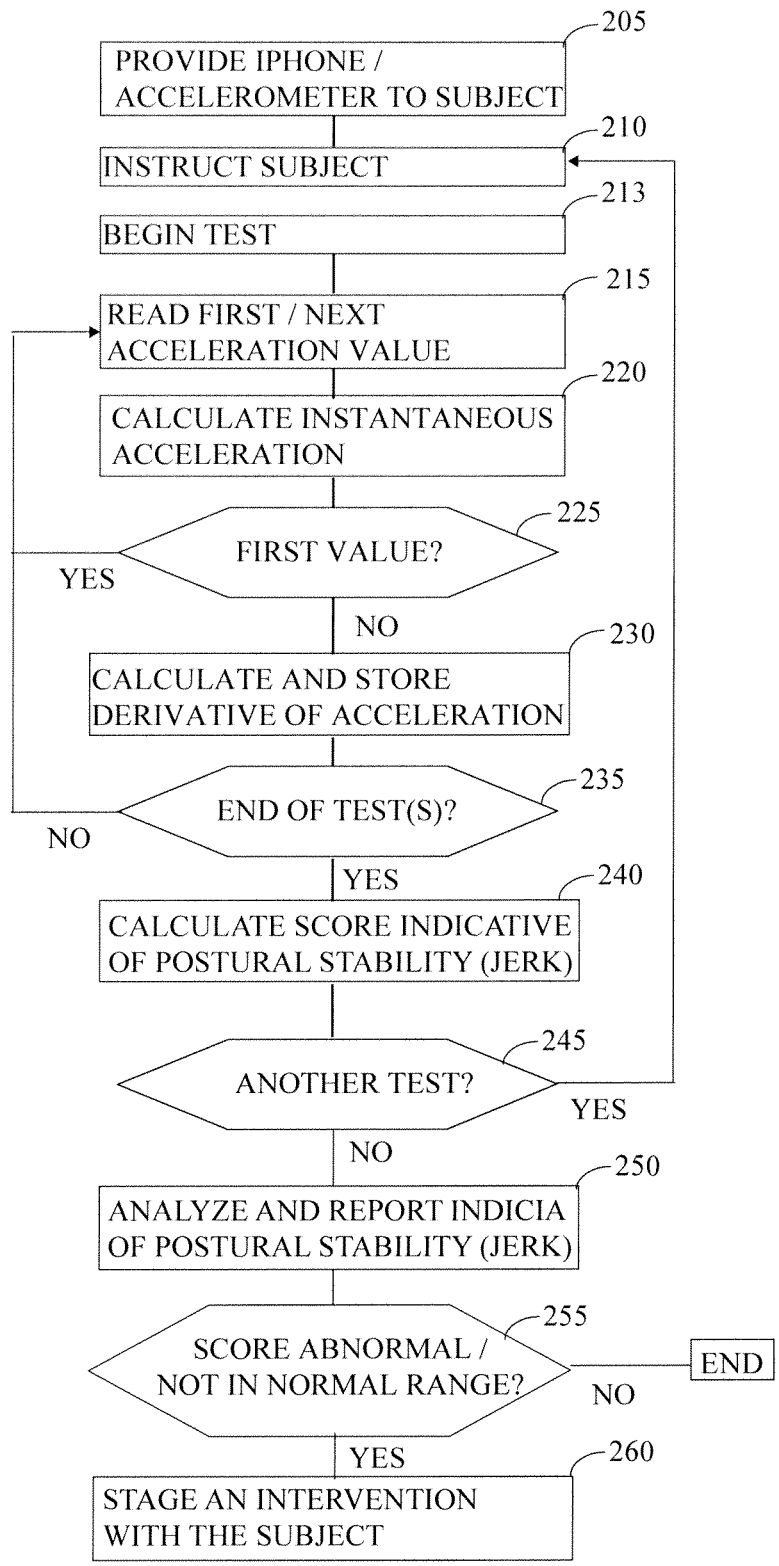
FIG. 2 contains a program operating logic suitable for use with the instant invention.

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments or algorithms so described.

An embodiment of the invention is a portable balance assessment tool that uses a self-contained tri-axis accelerometer, or other motion detection device, together with an associated microprocessor or other integrated CPU to measure thoracic body movement over time in order to evaluate stability. One embodiment uses single foot stance and tandem gait balance conditions, which are tested through the use of the instant handheld device, which is designed to measure parameters representative of compensatory thoracic sway. An embodiment of the inventive software uses a mobile application that is resident on an easily held hardware device (preferably the iPhone in this embodiment) to analyze movement characteristics of the device, which is securely held at chest level by a subject. The movements of the device in response to the subject's tests are analyzed and a "balance score" is computed as set out below.

In one embodiment, a cognitive assessment is combined with balance testing that includes simple and choice reaction times, working memory/information processing and delayed recall memory, etc. One goal of the cognitive tests is to assess both left hemisphere brain function with linguistics and right hemisphere brain function with information processing. These two test categories are combined with postural stability assessment (cerebellum function), to make it possible to more fully estimate function in all three major brain regions.

The human body can be divided into three distinct regions which move independently under unstable conditions: Foot Ground Contact (FGC), Waist or Center of Mass (COM) and above COM or Thoracic Sway (TS). Exaggerated force platform readings have been found during FGC measurements of healthy elite athletes according to research by the instant inventor. Force platform readings (which are conventionally known as the postural sway gold standard) showed more movements, and therefore more instability, in elite athletes than the normal population. This is likely due to exaggerated foot compensation in athletes that is used to maintain balance. This effect appears to be from trained proprioceptive feedback in the extremities, and increased stabilization in the joints above the FGC point (Knee, Hip, Lumbar, Thoracic). Compensatory movements in less balanced subjects appear to occur above the COM, most notably in the arms, head and trunk. Although these compensatory movements are most exaggerated in the arms and head, the movements are asymmetrical and disjointed from the central kinetic chain, making them unreliable in the evaluation of postural sway.

COM sway measurements, using accelerometer readings worn at the waist, are also potentially an ineffective measurement of postural sway, because the center of mass acts as a fulcrum for postural movements. Very little motion typically occurs at the COM, therefore it does not provide the optimal assessment location for determining changes in postural control.

One object of the invention in a current embodiment is to allow "healthy" individuals to establish normal function and retest following suspected proprioceptive impairment. The development of a large database of easily accessed, individualized balance scores will give each user a very accurate baseline or normal score. Accumulation of users' scores will also help develop population norms that can be used for comparative analysis.

An approach to balance assessment software in this embodiment includes three variables:

a. Location of measurement—The specific body region targeted (anterior trunk-collarbone to abdomen). The approach of an embodiment of the instant invention which utilizes accelerometers for the purpose of postural sway or movement assessment has not previously been taught.

b. Testing Protocol—Testing a subject with a server connected hardware device securely pressed against his or her anterior trunk with testing protocols that might include performance-based tests such as Static Postural Sway, Tandem Stance, Tandem Gait, Single Leg Stance, Dynamic Squat, Single Leg Squat, Step up Test, Up and Go Test, Jump Stability. A key element to the testing protocol is the real time (or near real-time) sensing, recording, and analysis of data on the testing device itself to provide instantaneous analysis of the procedure without computer connectivity or delayed analysis.

c. Stability Algorithms—Finally, the instant invention in some embodiments uses custom software algorithms to analyze the subject's movement patterns and issue a balance score.

An approach according to the instant invention that utilizes thoracic sway measurements with a handheld device, instead of using expensive force platforms to measure FCG movements or poorly placed accelerometers that must be worn or fixated and analyzed later, presents a preferred way to analyze changes in balance. The replacement of "worn" accelerometers in poorly placed locations (waist, head or arms), with software developed for a hand held device that most users currently own and use daily, makes the instant approach to balance assessment a superior assessment tool for low cost administration.

The assessment of postural stability is performed according to an embodiment of the instant invention by using proprietary algorithms that evaluate the instantaneous acceleration readings that are acquired from an accelerometer (e.g., the LIS302DL MEMS accelerometer) or gyroscope of the sort that is typically built into a hand-held devices such as an iPod Touch, an iPod Nano (4$^{th}$ and 5$^{th}$ generation), and a wide variety of cell phones including the Apple iPhone, certain Blackberry cell phone models, certain Nokia cell phone models, and many others As is generally indicated in FIGS. 1A, 1B, and 1C, in an embodiment, subjects are instructed to use both hands to clasp the hand-held accelerometer equipped device 100 against their chest, after which they will preferably be instructed to perform one task or a sequence of progressively more difficult balance tests while the instant Sway Balance system analyzes postural variables via the accelerometer in the device 100.

The readings from the accelerometer will then be used to provide a numerical/quantitative indication of the subject's balance during the task(s) and, in some embodiments, a representation of balance on a scale of 0-100 will be obtained. For example, a test subject might be presented with a drawing FIG. 1A on the screen of an iPhone and asked to stand for some period of time on one foot (i.e., a single foot stance). In other instances, a drawing similar to that in FIG. 1B might be presented to the user along with the instructions that he remain as motionless as possible in a standing position. In other instances, the user might be shown an image like that in FIG. 1C and stand with his feet in tandem or to walk some number of steps (or for some time period) in a straight line. In each case, during the test the accelerometer will be read continuously, with the resulting data used as is described below.

Turning next to FIG. 3, a preferred hardware aspect 100 of the instant invention will include a CPU 105 (microprocessor, computer chip, etc.) and some amount of volatile or nonvolatile memory 110 (collectively "memory", hereinafter) into which program instructions and accelerometer readings may be stored and from which they may be recalled again. In this embodiment, CPU 105 will be in electronic communication with a tri-axis accelerometer 115 and with a display device 120 which will preferably be integral to the device 100. In some embodiments, the display device 120 will be used to communicate to the subject information such as task instructions, test results, etc. The inventive device 100 in some embodiments will include a hardware port 125 to allow electronic communication with the device 100 when it is docked with a laptop or desktop, etc. The port 125 might be, by way of example only, a USB port, a Firewire port, a proprietary interface port (e.g., the Apple® iPhone® 30 pin connector), etc. In other embodiments, the hand-held device 100 might have a Bluetooth, WiFi, cell phone, or other communications device to allow the CPU 105 to communicate wirelessly with a remote computer 150.

In some embodiments the results of previous balance tests for this same subject can be accessed on the mobile device itself with an interactive graphical representation of current and previous scores. Detailed group and organizational analyses can be accessed through, for example, a web portal that would make it possible to receive test data and analyze it in order to identify important trends within a population. The web portal will be configured to provide a rich database for evaluating the effectiveness of implemented interventions, the difference between subjects taking alternative medications, or any potential differentiator that could have an impact on balance.

In an embodiment, the measured quantity that is used to determine the amount of subject movement is referred to as JERK (m/s3 or g/s), which is the change in acceleration or the derivative of acceleration with respect to time. This value is used to estimate the amount of movement, or lack of movement, in order to determine the stability of the subject. In this embodiment, by taking the summation of the absolute value of the instantaneous acceleration at two different time points, a Jerk score can be computed. In one embodiment, the Jerk score over some period of time will be calculated via the formula:

$$\text{JERK} = 0.1 * \left[ \sum_{i=2}^{N} |X_i - X_{i-1}| \right],$$

where $X_i$ is instantaneous acceleration recorded at time point "i". That is, $X_1$ is the initial instantaneous acceleration in the vertical direction as recorded at a first time point, $X_2$ is the instantaneous acceleration recorded at some later time time point "2", etc. In some embodiments, the interval between successive measurements will be 0.1 seconds, although the selection of other time intervals (including non-uniformly spaced time intervals that might be used, for example, to sample more frequently when the subject is moving more rapidly) is certainly possible and well within the ability of one of ordinary skill in the art. In some embodiments N, the number of instantaneous acceleration measurements, will be 100 and the instantaneous acceleration will be measured over a period of 10 seconds.

In a preferred embodiment, the acceleration will be determined as deviation from the vertical gravity vector of −9.8 m/s$^2$ or −1 g-force. That is, if the accelerometer (e.g., the sort of one found in an iPhone) or other measuring device is held still and completely vertical, the acceleration will be a −1 g-force in the "Y" axis direction due to gravity and 0 g-force for the X and Z axes. In some preferred embodiments, the instantaneous acceleration will be adjusted to eliminate the effect of gravity, which can be assumed to be a constant. Any tilt or movement in the measuring device will be reflected in a change in the instantaneous acceleration, which will be represented as a higher JERK value.

In a preferred embodiment, a recording frequency of 10 hertz over a 10 second period will provide 99 changes in instantaneous acceleration, providing 99 JERK scores for each of the three directional axes (medial-lateral ("ML") or X-axis, anterior-posterior ("AP") or Z-axis, and superior-inferior ("SI") or Y-axis). The 99 Jerk scores may be filtered based on a sensitivity threshold, normalized and sorted for paired samples comparison, analyzed by taking the sum, standard deviation, skewness, variability, correlation or any number of other established statistical evaluation of the data in order to provide a total stability score for a preferred 10 second test period.

In some embodiments, an acceleration threshold will be applied to eliminate "jitter" or small deviations in acceleration that could be due, for example, to the limits of measurement accuracy of the accelerometer. That is, depending on the hardware even if an accelerometer is kept perfectly still (e.g., it is resting on a table) in some instances it will still report minute instantaneous acceleration changes. Thus, in some embodiments the manufacturers sensitivity values that have been reported for MEMS or other brand accelerometers will be subtracted from each JERK value to ensure that movement occurring at each point in time is dependent upon device movement alone and is not biased by potential sensitivity variations and recording errors. As a specific example, the device sensitivity of the current version of the iPhone accelerometer has been reported to be 0.0196 g-force per measurement and, as such, it might be useful to discard any measured acceleration changes that are smaller than this number and to only analyze the values that are more clearly a result of device movement by the user.

In some embodiments, following completion of a test battery, the user will be provided with a balance score based on the conditions performed, which may be immediately compared to user selected population normative values. The analysis of normative data from a live synched server provides a rich database for comparison of balance scores to self-selected peers. This interactive database of balance scores is novel in the balance assessment market, as previous comparison tools use outdated normative values that do not adjust and do not allow the user to more accurately compare to their self-selected peer group.

The balance score set out above has been developed using motion assessment of all three directional axes and over multiple conditions for a given protocol. In an embodiment, the single balance score may be compared with previous test results, which previous test results can be used to establish a baseline for a given subject. A baseline might be given as an "overall score" or average balance score for all baseline tests, and a "normal range" which will be a provided in some embodiments, which normal range might be based on the number of tests taken and the variability of the tests taken previously. In an embodiment, statistical confidence intervals will be used to establish the normal range associated with each user. In some cases, to establish an adequate baseline the subject may be asked to perform four trials of a given protocol. In some embodiments, the confidence intervals will be based on data have been acquired from multiple subjects, preferably subjects that are comparable in some sense (e.g., within the same age range, participants in the same sporting activity (e.g., football players), etc.).

The "current score" that might be provided to the user will typically be the most recently administered test score and can be compared to the "normal range" to determine if it falls outside of the confidence interval and therefore should be red flagged as a "likely impaired" test result. Preferably, the subject will be asked to retake the balance test following a failed test (one that is outside the normal range) to ensure that the failed test is not just an outlier.

Turning next to FIG. 1, according to a preferred embodiment of the instant invention, the drawings depict the placement of the handheld device in its current embodiment and three testing protocols (standing sway, tandem stance, single foot stance) that users might be asked to perform. Users are instructed to place the device against their chest directly under their collarbone and then perform a balance test based on a given protocol.

FIG. 2 contains an operating logic suitable for use with the instant invention. According to one embodiment, a first step will be to provide an accelerometer/CPU combination (to include providing an iPhone or other readily available device) to the subject (step 205). Broadly speaking there are two instances in which the subject might be tested. First, the subject might be tested during a period when he or she is believed to be functioning normally in order to obtain, for example, baseline measurements from one or more tests for later comparison with a subsequent test by the same or a different subject. A second instance when the subject might be tested, of course, would be in cases where the subject has experienced some sort of incident or intervention that might impair that subject's balance.

Next, preferably the subject will be instructed as to which test will be performed and how to perform such a test (step 210). Of course, this step might be delivered verbally by the test administrator or via instructions delivered via computer (e.g., displayed on the face of the cell phone) or printed instructions. One component of those instructions will be to require that the subject take the accelerometer in hand and hold it firmly against his or her upper torso (e.g., chest) as is generally indicated in FIGS. 1A-1C.

The accelerometer will then be readied (e.g., the sensing and recording program might be activated by the test monitor or the subject) and the subject asked to begin the current test (step 213).

As the subject performs the test, the instant invention will continuously read (step 215) values from the three-component accelerometer that is preferably a part of the measuring device, where "continuously" means at closely spaced time intervals. As has been indicated previously, one sample interval suitable for use with the instant invention is 0.1 second spacing or ten times a second. Clearly, other sampling intervals (sample rates) could readily be used and those of ordinary skill in the art will readily be able to adapt the foregoing when the sample rate is higher or lower than the examples given herein.

Next, and preferably, the instantaneous acceleration ($X_i$) will be calculated from the three-component measurement that is a part of the preferred hardware component (step 220). Next, and preferably, a numerical estimate of the derivative of the acceleration (JERK) will be calculated. A preferred way to do this calculation requires at least two successive measurements hence, in the example of FIG. 2, the derivative step (230) will not be reached until there are at least two values available to use in the computation. Note that, although the example of FIG. 2 suggests that the derivative might be calculated in real (or near-real) time as the data values are collected, obviously that could be done at any point including after the testing has been concluded.

Next, and continuing with the example of FIG. 2, if the test is not at an end (the "NO" branch of decision item 235), the preferred operating logic will branch back to the start and begin data collection again. Otherwise, the numerical value of the JERK coefficient will preferably be calculated (step 240).

In some embodiments, the subject may be asked to perform either a different test or repeat the same test (decision item 245). If that is the case (the "YES" branch of this decision item), the operating logic will preferably branch again to the top and the subject will be instructed again, etc.

Otherwise, the instant invention will preferably analyze and report the data collected (step 250) and stop. In some embodiments, as has been discussed previously, the JERK coefficient(s) or a similar indicium of the user's postural sway and/or stability during the test(s) will be compared with a baseline measurement for that same subject or with a population norm. In an embodiment, the indicium or indicia will be presented to the subject by displaying a message on display of the instant testing device 100 that indicates that the subject has been shown to have normal or abnormal postural stability, as the case may be (e.g., "PASS" or "FAIL"). In some instances, the JERK coefficient will be reported, without or with some measure of how it compares with the baseline measurement or population norm (e.g., the subject's score might be shown as a point on a standard normal distribution, compared with the mean/standard deviation of the population, etc.). Those of ordinary skill in the art will readily be able to devise reports to communicate the test results to the subject, which test results might appear on the testing device 100 and/or elsewhere.

Finally, in some embodiments if the subject's score is within normal limits (the 'NO' branch of decision item 255), the instant invention will terminate. In some embodiments, users that are within plus or minus two standard deviations (or three, etc.) of the average for subjects of the same general type will be determined to be "normal". In other instances, the subject will be determined to be "normal" if the currently measured score is within the range defined by previous measurements of the same subject (e.g., that subject's baseline measurements).

Otherwise, (the "YES" branch), when an abnormal, questionable or out of range score is reported an intervention will be staged. In the case that the subject is a football player, the intervention might consist of preventing the player from returning to the game and sending him or her to a medical station for further testing to determine whether or not that individual has experienced a concussion. If the test subject is, for example, elderly, the intervention might consist of sending the subject to additional testing for Alzheimer's disease, dementia, etc. Finally, where the results are questionable (e.g., in instances where the subject does not understand or refuses to follow instructions), the intervention might consist of asking the subject to retake the test(s), determining that the subject is not within normal limits, etc.

Other potential embodiments of the invention could include using trunk movement analysis in other stable or unstable environments that could be static (as described in the single foot stance of the current invention) or dynamic (as described in the tandem gait condition). The use of anterior trunk movement analysis could also pertain to functional conditions such as to evaluate consistency of training movements (squat, jump, running, cutting) or detailed analysis of sport specific movements (throwing a football, shooting a basketball, dribbling a soccer ball, specific martial arts kicks or punches) where the device may be fixated instead of held, to the anterior trunk. These examples are by no means exhaustive, but rather examples of specific movements to portray intent of evaluation.

Not only does the further evaluation of movements in sport present a potential use for this invention, but also balance evaluation in other populations such as a tool for Alzheimer's screening, Chemobrain analysis, occupational function screening, drug and sobriety test, drug and pharmaceutical testing, sports concussions, physical therapy/orthopedic injury and any other condition or environment where trunk movement, vestibular function or balance could be tested.

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those skilled in the art, without departing from the spirit of the inventive concept the scope of which is to be determined by the following claims.

What is claimed is:

1. A method of assessing a subject's postural stability, wherein is provided a hand-held three-component accelerometer, comprising the steps of:
    (a) providing the three-component accelerometer to the subject;
    (b) instructing the subject to clasp with a hand the three-component accelerometer against an upper torso of the subject;
    (c) instructing the subject to perform a task while the three-component accelerometer is so clasped;
    (d) continuously recording an output of said accelerometer during the subject's performance of said task, thereby obtaining a plurality of three-component accelerometer measurements during the performance of said task;
    (e) determining from at least a portion of said plurality of three-component accelerometer measurements a JERK score indicium representative of the subject's postural stability, wherein said JERK score is calculated according to the equation:

$$\text{JERK} = 0.1 * \left[ \sum_{i=2}^{N} |X_i - X_{i-1}| \right],$$

where $X_i$ is an instantaneous acceleration recorded from said three-component accelerometer at time point "i",
    where $X_{1-1}$ is an instantaneous acceleration recorded from said three-component accelerometer at time point "i-1", and,
    where "N" is the total number of instantaneous accelerations recorded during said task;
    (f) using at least said indicium to determine whether the subject's postural stability is within a normal range;
    (g) if the subject's postural stability is within said normal range, taking no further action with respect to the subject; and,
    (h) if the subject's postural stability is not within said normal range, staging an intervention with respect to the subject.

* * * * *